(12) United States Patent
Koblizek et al.

(10) Patent No.: US 9,701,954 B2
(45) Date of Patent: Jul. 11, 2017

(54) METHOD AND DEVICE FOR UNIFORMLY TREATING ADHERENT CELLS

(75) Inventors: Thomas Koblizek, Goettingen (DE); Andreas Heinze, Cologne (DE); Timo Gleissner, Euskirchen (DE); Herbert Mueller-Hartmann, Cologne (DE); Andreas Wirth, Weidenberg (DE)

(73) Assignee: LONZA COLOGNE GMBH, Cologne (DE)

( * ) Notice: Subject to any disclaimer, the term of this patent is extended or adjusted under 35 U.S.C. 154(b) by 387 days.

(21) Appl. No.: 13/806,395

(22) PCT Filed: Jun. 21, 2011

(86) PCT No.: PCT/EP2011/060349
§ 371 (c)(1),
(2), (4) Date: May 22, 2013

(87) PCT Pub. No.: WO2011/161106
PCT Pub. Date: Dec. 29, 2011

(65) Prior Publication Data
US 2013/0230895 A1  Sep. 5, 2013

(30) Foreign Application Priority Data
Jun. 22, 2010  (EP) .................................... 10006458
Dec. 23, 2010  (EP) .................................... 10015997

(51) Int. Cl.
| C12M 1/42 | (2006.01) |
|---|---|
| C12N 13/00 | (2006.01) |
| C12M 1/32 | (2006.01) |
| C12N 15/87 | (2006.01) |
| A61N 1/32 | (2006.01) |

(52) U.S. Cl.
CPC ............ *C12N 13/00* (2013.01); *C12M 23/12* (2013.01); *C12M 35/02* (2013.01); *C12N 15/87* (2013.01); *A61N 1/327* (2013.01)

(58) Field of Classification Search
CPC ......... C12M 35/02; C12N 15/87; A61N 1/327
See application file for complete search history.

(56) References Cited

U.S. PATENT DOCUMENTS

| 5,134,070 A | 7/1992 | Casnig |
|---|---|---|
| 5,273,525 A | 12/1993 | Hofmann |
| 5,869,326 A | 2/1999 | Hofmann |
| 6,352,853 B1 | 3/2002 | King et al. |
| 7,062,310 B2 | 6/2006 | Bernhart et al. |
| 8,101,401 B2 | 1/2012 | Muller-Hartmann et al. |
| 8,994,382 B2 | 3/2015 | Nielsen et al. |
| 2002/0164776 A1 | 11/2002 | Beichmann et al. |
| 2003/0157708 A1 | 8/2003 | Ozaki |
| 2005/0089991 A1 | 4/2005 | Walters et al. |
| 2007/0105214 A1 | 5/2007 | Micklash et al. |
| 2009/0305380 A1 | 12/2009 | Ragsdale |
| 2010/0021038 A1 | 1/2010 | Schulz |
| 2010/0249771 A1* | 9/2010 | Pearson ............. A61B 18/1206 606/34 |

FOREIGN PATENT DOCUMENTS

| CN | 1889886 A | 1/2007 |
|---|---|---|
| CN | 1930280 A | 3/2007 |
| CN | 101421913 A | 4/2009 |
| CN | 101558147 A | 10/2009 |
| JP | 01-112787 A | 5/1989 |
| JP | 01-235576 A | 9/1989 |
| JP | 02-131584 A | 5/1990 |
| JP | 10-234366 A | 9/1998 |
| JP | 2003-144136 A | 5/2003 |
| JP | 2004 202086 | 7/2004 |
| JP | 2005-261323 A | 9/2005 |
| JP | 2010-022360 A | 2/2010 |
| WO | 00/23563 A1 | 4/2000 |
| WO | 2005/056788 A1 | 6/2005 |
| WO | 2005056778 | 6/2005 |
| WO | 2007/094947 A2 | 8/2007 |
| WO | 2008104086 A1 | 9/2008 |
| WO | 2009/131972 A1 | 10/2009 |
| WO | 2009131972 A1 | 10/2009 |
| WO | 2009/140161 A1 | 11/2009 |

OTHER PUBLICATIONS

Lin et al. "Simulation and experimental demonstration of the electric field assisted electroporation microchip for in vitro gene delivery enhancement." (2004) Lab Chip, vol. 4, : 104-108.*

(Continued)

*Primary Examiner* — Louise Humphrey
*Assistant Examiner* — Teresa E Knight
(74) *Attorney, Agent, or Firm* — Joyce von Natzmer; Agris & von Natzmer LLP

(57) ABSTRACT

The invention relates to a method for subjecting adherent cells to at least one electric field, in which the electric field is generated by applying a voltage to at least two active electrodes 63, wherein at least three electrodes 63, 64 are provided, and wherein at least two electrodes 63, 64 are active electrodes 63 when the voltage is applied in order to generate a first electric field, and in which at least one second electric field is generated, wherein at least one of the two previously active electrodes 63 is a potential-free electrode 64 when the voltage is applied. The invention further relates to a device 58 comprising at least three electrodes 63, 64, which are connected to at least one voltage source by means of at least one switching device 59, 60, 61, 62, wherein at least five electrodes 63, 64 are connected to the at least one voltage source by means of four switching devices 59, 60, 61, 62, wherein at least two electrodes 63, 64 are connected to the voltage source by means of a common switching device 59, 60, 61, 62. In conjunction with the method described above, the device according to the invention allows the efficient and uniform treatment of adherent cells using an electric field, wherein the switch between active and potential-free electrodes can be carried out quickly and safely using a lower number of switching devices.

6 Claims, 15 Drawing Sheets

(56) References Cited

OTHER PUBLICATIONS

Database WPI Week 200449, Abstract XP002610220, Thomson Scientific, London, GB; AN 2004-514495 (Jul. 22, 2004).
"Petri Pulser Electrode User's Manual," BTX Harvard Apparatus, retrieved Mar. 26, 2013, at http://www.btxonline.com/content/PDFS/UserManuals/Petri_Pulser_Electrodes_0908.pdf (closest found to catalog found Nov. 2010).
Lin, Y.C. et al., "Simulation and experimental demonstration of the electric field assisted electroporation microchip for in vitro gene delivery enhancement." Lab Chip (2004) vol. 4, pp. 104-108.
NPL pdf "CUY900-13-3-5 Technical_Drawings" of webpage at http://www.sonidel.com/sonidel/%20cuy900-13-3-5_technical_drawings/ accessed Jun. 13, 2014.
NPL pdf "nepagene electrodes" of webpage at http://www.bulldog-bio.com/nepagene/Electrodes.pdf accessed Jun. 13, 2014.
NPL pdf document "JP 2004-202086 Japanese Patent Office English machine translation" downloaded from Japanese Patent Office at http://www4.ipdl.inpit.go.jp/Tokujitu/tjsogodbenk.ipdl; accessed Jun. 13, 2014.

\* cited by examiner

A)

B)

C)

A)

B)

A)

B)

METHOD AND DEVICE FOR UNIFORMLY TREATING ADHERENT CELLS

CROSS-REFERENCE TO RELATED APPLICATIONS

This is the U.S. national stage of International application PCT/EP2011/060349, filed Jun. 21, 2011 designating the United States and claiming priority to European applications EP 10006458.3, filed Jun. 22, 2010 and EP 10015997.9, filed Dec. 23, 2010.

BACKGROUND OF THE INVENTION

The invention relates to a method for applying at least one electric field to adherent cells, in which the electric field is generated by applying a voltage to at least two active electrodes, wherein at least three electrodes are provided. The invention further relates to a device comprising at least three electrodes which are connected to at least one voltage source via at least one switching device. The invention also relates to a device for contacting at least two electrode arrangements which each comprise at least two electrodes, wherein at least two electrode arrangements have different dimensions and wherein the device includes contact elements by means of which an electrical contact can be made to the electrodes of the electrode arrangements.

PRIOR ART

Application of an electric field or voltage pulse to living cells, so called electroporation or electrotransfection, is practiced for years on cells in various states. As single cells in suspension in a buffer solution, at adherent state in a culture container, usually at the bottom of a plastic container, and in vivo where cells usually are embedded in a tissue assembly of an extracellular matrix. In principle in electroporation foreign molecules are introduced into the cell from a buffer solution, which is adapted to the cells, or a cell culture medium by applying a short-term current flow, whereby the cell membrane are made permeable for the foreign molecules due to the action of electric voltage pulses or the thereby resulting electric filed and current flow. The cell suspension are placed often in a so called cuvette, that is a narrow, open container, which sample chamber has two opposite, parallel electrodes in the side walls, which serve for applying electric voltage. By the temporary emerging "pores" in the cell membrane the biologically active molecules first reach the cytoplasm, where the molecules possibly already are able to perform their function of interest and then under certain conditions as well the nucleus. Due to short-term application of a strong electric field, that is a short voltage pulse of a high current density, in addition cells, cell derivatives, subcellular particles and/or vesicles may also be fused. In the so called electrofusion, for example, the cells first are brought into close membrane contact by an inhomogeneous alternating electric field. By subsequent application of an electric field pulse then interaction of membrane parts occur, which finally results in fusion. For electrofusion thereby comparable apparative devices as for the electroporation are applicable. Moreover living cells may be stimulated by electric field even in a manner changing their properties.

From WO 2005/056778 A1 for example a method for electroporation is known, in which cells are growing on a microporous membrane located between two parallel arranged electrode surfaces.

U.S. Pat. No. 5,134,070 describes applications and devices for electroporation of cells, which are growing on an electrically conductive surface, which serves as electrode. The culture container is covered from above with a plate-shaped counter electrode, whereby a gap is formed across that electric discharge is possible.

Moreover from WO 2008/104086 A1 a device is known, in which cells are growing on co-planar electrode surfaces. The electrical contact between the electrodes is established by the cell culture medium above the cells, whereby the two electrode regions are separated by an isolating barrier, but which nevertheless allows an electrolyte bridge between the electrodes. That for example can consist of indium tin oxide, which as a transparent semiconductor allows microscopic analyses of the cells.

From WO 2009/131972 A1 a device for electroporation of cells, which are growing adherent on a round disc-shaped plate, is known. The device exhibits two electrodes arranged parallel to each other, whereby one electrode is located on the concave surface of an external cylinder and the other electrode on the convex surface of an internal cylinder.

Moreover from US 2009/0305380 A1 a device for electroporation of cells, which are immobilized on a solid area, is known. The electric field, which is applied to the cells, is generated by an arrangement of electrode pairs, which are located lying closely next to each other on a surface above the solid area. The electrodes are formed by means of electric rails, which are plated on the surface. Both electrodes of one electrode pair are thereby arranged as close to each other that not more than one single cell can be located within the smallest distance between both electrodes.

The company BTX distributes as PetriPulser® an arrangement of alternating poled coplanar electrode plates, which can be applied vertically on adherent growing cells in a culture container. Thereby the electrodes immerse into the culture supernatant, whereby the spaces between the individual electrode plates are filled with culture medium. A significant disadvantage of this arrangement is that a major part of the current leaks in the cell free culture medium above the cells. But this field is only effective at the border area on the bottom of the container, where the cells are located, so that unnecessary high currents have to be provided. Moreover, high mortality has to be assumed because of pH-value changes and high current. Furthermore, the power supply for long term voltage pulses has to be strong enough to provide those high currents and thus charges and powers. Moreover, a large volume has to be provided, which is suitable for electroporation and which comprises the substrate to be transfected at sufficiently high concentration, whereby the amount of the substrate is correspondently higher as well. It is a significant disadvantage of this known device that the electric field has minimum strength within the region located orthogonally below the free electrode tips. Consequently, the cells present in this region are actually not transfected or fused so that efficiency of the processes employed by means of this known device is low altogether.

DESCRIPTION OF THE INVENTION

It is the object of the invention to provide a method and device enabling an efficient and uniform treatment of adherent cells using an electric field.

According to the invention, the object is achieved by a method of the initially mentioned kind, in which at least two electrodes are active electrodes when the voltage is applied for generating a first electric field, and at least a second electric field is generated, wherein at least one of the two former active electrodes is a floating electrode when the voltage is applied. If, for example, a first electrode is active, i.e. either positive or negative pole, when a voltage pulse are applied to the cells, the electric field underneath this electrode has minimum strength so that the cells orthogonally located underneath this electrode are not sufficiently electrically treated. Consequently, according to the invention a second electric field is generated wherein said first electrode is now floating (passive). That is, the electric field is generated by applying a voltage to at least two different electrodes. It is thus achieved that during the second voltage pulse the electric field is now applied also to the region underneath said first electrode. As a result, the method according to the invention ensures that also the cells that were not exposed to an electric field during the first voltage pulse are sufficiently electrically treated as well. By means of the method according to the invention the number of regions within which the electric field is low can be effectively minimized so that efficiency of the respective process, e.g. an electrotransfection or electrofusion, may be optimized. The method according to the invention is therefore advantageously suitable to ensure an efficient and uniform treatment of adherent cells by an electric field.

Preferably, as many electric fields as necessary are generated during generation of further electric fields to make at least once floating electrodes out of all electrodes that have been active when the first electric field was generated. In this manner, it is ensured that no regions which have not been exposed to an electric field are present underneath the electrodes. Accordingly, in this optimal case all cells are uniformly treated by an electric field so that in the respective process, e.g. an electrotransfection or electrofusion, maximum efficiency may be ensured.

In another preferred embodiment of the invention it is provided that each electrical field is respectively generated by at least one voltage pulse, preferably at least two voltage pulses. According to the invention, the electric fields each may be generated by a single voltage pulse or at least two or many shortly succeeding or merging (sub-) voltage pulses. Thereby, the sub-pulses may be generated by discharging one or more electric charge storage(s), preferably one capacitor or at least two capacitors. Preferably, each voltage pulse generating an electric field is a double pulse being composed of a short high voltage pulse and a longer pulse of relatively low voltage. Such double pulse may be generated, for example, by successively discharging two capacitors, one shortly after the other wherein both sub-pulses may merge without interruption. For instance, a first electric charge storage unit may have a capacitance of at least 10 µF, preferably at least 50 µF, in particular at least 100 µF, and/or may be discharged at an initial voltage of 10 to 1500 V, preferably 20 to 1200 V, in particular 50 to 1000 V, with a pulse length 2 µs to 40 ms, preferably 5 µs to 20 ms, in particular 10 µs to 10 ms. Shortly before, concurrently with or shortly after the end of the discharge of the first electric charge storage unit a second electric charge storage unit, for example, having a capacitance of at least 100 µF, preferably at least 500 µF, in particular at least 1000 µF, may be discharged at an initial voltage of, e.g., 10 to 240 V, preferably 20 to 200 V, in particular 50 to 150 V, with a pulse length of, e.g., 1 ms to 500 ms, preferably 2 ms to 350 ms, in particular 4 ms to 250 ms.

Concomitantly or alternatively, the at least two electrical fields may respectively be generated by at least one voltage pulse wherein the time gap between the voltage pulses is at least 500 ms, preferably at least 1 s, in particular 1 to 10 s. Surprisingly, the time gap between the voltage pulses (not sub-pulses!), which each generate an electric field as defined by the invention, has to be relatively large so as to keep the survival rate of the cells stable and/or ensure high efficiency of the process. Thereby, as described above, each single voltage pulse may be composed of multiple, i.e. at least two, sub-pulses.

In a further preferred embodiment of the invention it is provided that several reaction spaces are provided within which the electric fields are respectively applied to adherent cells, wherein the time gap between two voltage pulses for generating two electric fields within one reaction space is utilized to generate at least one electric field within at least one further reaction space. This embodiment of the invention is particularly advantageous if many samples have to be treated within a very short period of time, that is, in particular in high throughput processes. As already described above, the single voltage pulses for generating the electric fields within the respective reaction spaces may have a relatively long temporal distance to each other. If many samples are processed, this would result in very long process duration. According to the invention, the single voltage pulses are thus generated in a preferably nested manner in respect of the different reaction spaces to be treated, so that the dead time between generations of two electric fields within one reaction space may be utilized for generating at least one electric field within at least one further reaction space. In this manner, the total process duration can be significantly reduced, e.g. in treating all reaction spaces of "24-well" cell culture plate. Moreover, by this approach the risk of occurrence of discrepancies between samples in different reaction spaces due to different incubation times before and/or after treatment is reduced. For instance, if the cells within the single reaction spaces of a "24-well" plate would be treated successively over a longer period of time, the samples within the first reaction spaces would run through a relatively long incubation period after the treatment while the lastly treated samples would have to run through a longer incubation period before the treatment. This may affect the efficiency of treatment within single reaction spaces and finally lead to different results with single samples. In contrast, nested treatment of different reaction spaces results in more consistent and hence more reproducible results and efficiencies, respectively, due to minimization of different incubation periods.

In a particularly preferred embodiment of the invention it is further provided that the electrodes and the adherent cells are separated from each other and that the distance between the cells and the electrodes is adjusted to an empirically determined value. Preferably, the distance is adjusted such that the strength of the electric field between the active electrodes and underneath the floating electrodes is respectively optimized. It was demonstrated that the density of the lines of electric flux decreases when the distance increases, so that the effective electric field on the bottom area of the container decreases when the distance increases. Technically, this effect might be compensated by increasing the voltage applied, i.e. by increasing the current density. However, this would increase the technical effort and the risk of lightning discharges. Too small distances make no sense either because even minor unevenness of the bottom surface would then result in inhomogeneity of the electric field and hence in non-reproducible results. In this context it has to be considered as well that the field strength between the active electrodes decreases when the distance increases while the field strength underneath the floating electrodes reaches a maximum value at a medium distance, i.e. decreases based on this maximum value when the distances decrease or increase. Therefore, depending on the conditions of the process, the distance of the electrodes to the cells has to be adjusted such that the field strength underneath the floating electrodes almost reaches the maximum value and concurrently reaches a value between the active electrodes that is as high as possible. This optimal distance has to be empirically determined for different conditions such as geometry of the reaction space, type of used buffer solution, shape and size of the electrodes, and electrical parameters.

According to the invention, the object is also achieved by a device of the initially mentioned kind, in particular a device for accomplishing the method according to the invention, wherein at least five electrodes are connected to the at least one voltage source via four switching devices, and wherein at least two electrodes are connected to the voltage source via a shared switching device. Due to this particularly advantageous configuration all electrodes may be operated as active or passive (floating) electrodes. By grouping of electrodes and limiting the number of switching devices in the device according to the invention the technical and constructional effort is minimized so as to provide a cost-effective device being less prone to interferences. In connection with the above-described method the device according to the invention allows for efficient and uniform treatment of adherent cells with an electric field, wherein switching between active and floating electrodes may be accomplished fast and secure using a low number of switching devices.

In a particularly advantageous embodiment of the device according to the invention it is provided that two groups of electrodes are provided, each of which being connected to the voltage source via two shared switching devices. By means of this a relatively high number of electrodes can be controlled by only four switching devices, i.e. each of both groups of electrodes may be operated as active or passive (floating).

Hereby, each group preferably comprises at least two electrodes, preferably at least three electrodes, particularly preferred at least four electrodes. In a preferred embodiment of the invention, a total of at least seven, preferably 9-21, electrodes are provided. For instance, according to the invention a configuration might be used in which a first group comprises 8 electrodes and a second group comprises 9 electrodes.

In an advantageous embodiment of the device according to the invention it is provided that the electrodes are provided for insertion into at least one reaction space, i.e. the electrodes may be, for example, arranged and designed as a unit such that they may be inserted into a cell culture container from above and dip into the cell culture medium situated therein, if applicable. The electrodes may then be disposed in an advantageous manner above the cells adhering to the bottom of the reaction space. Preferably, the reaction space is thereby part of a multiwell plate so that a plurality of samples can be treated by the device according to the invention under comparable conditions.

The switching devices may be, for example, power semiconductors, preferably IGBTs or MOSFETs, or electromechanical devices, preferably relays.

According to the invention, the object is further achieved by a device of the initially mentioned kind for contacting at least two electrode arrangements, wherein at least one contact element is disposed such that electrodes of the different electrode arrangements can be respectively contacted thereby. Thereby, the arrangement of the contact element/contact elements is carried out in an advantageous manner such that it takes/they take a position at which it/they can contact electrodes of at least two electrode arrangements having different dimensions. Thus, e.g., electrode arrangements for cell culture plates having different size, for example, "6-well" and "24-well" plates and/or "12-well" and "48-well" plates, can be contacted by a significantly lower number of contact elements, so that the constructional effort is reduced on the part of the device. In any case, using the device according to the invention material is conserved and constructional effort is minimized altogether.

In a particularly advantageous embodiment of the device according to the invention it is provided that at least a part of the contact elements is disposed such that at least 50%, preferably at least 60%, in particular at least 70%, of the electrodes of the different electrode arrangements can be respectively contacted thereby. In the optimal case, the arrangement of the electrodes is identical for different plate dimensions. However, even if this should not be possible due to the geometry of the electrode arrangements, with the device according to the invention at least half of the electrodes of different electrode arrangements may be respectively contacted by a shared contact element. Thus, the number of contact elements necessary on the part of the device may be significantly reduced altogether.

Preferably, the contact elements and/or the electrodes are arranged in-plane and pivotable around one axis so as to bring the arrangement of contact elements suitable for the respective reaction spaces and/or the corresponding electrode arrangement into the correct position by turning the arrangement, e.g. by 180°.

The invention further relates to the use of the device according to the invention for applying at least one electric field to adherent cells, in particular for electroporation and electrofusion of adherent cells.

The invention is further exemplarily described in detail with reference to the figures.

DESCRIPTION OF EXEMPLARY AND PREFERRED EMBODIMENTS

Figure 1:
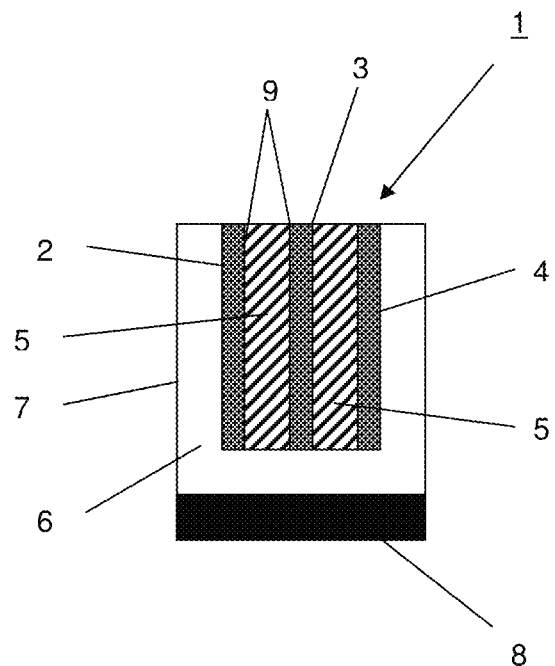
FIG. 1 shows a schematic side view of an electrode arrangement of an exemplary device according to the invention having three electrodes.

FIG. 1 shows an electrode arrangement 1 according to the invention comprising three coplanar electrodes 2, 3, 4 extending into the inner space 6 of a container 7. The container 7 comprises a bottom area 8 on which living cells may adhere and grow (adherent cells). The inner space 6 is usually filled with a liquid, e.g. a cell culture medium or another solution adapted to the cells. The space between the electrodes 2, 3, 4 is completely filled with an isolating material 5 so that no current may flow via the space located between the electrodes 2, 3, 4 if a voltage is applied to the electrodes 2, 3, 4. In the device according to the invention, the entire current flows through the space between the electrodes 2, 3, 4 and the bottom area 8 so that here voltage drops at a slower rate if a non-permanent voltage source (e.g. capacitor) is used and hence the field strength for treating the cells is higher over time. As a result, on the one hand the device for generating pulses can be economically dimensioned and on the other hand stronger changes of the pH value in the liquid, which would otherwise be induced by high amounts of charge flow resulting from electrolysis, may be avoided.

In the exemplary embodiment depicted here, coplanar electrodes 2, 3, 4 are separated from each other by an isolating material 5 so that electrically conductive surfaces of the electrodes 2, 3, 4 are only exposed downwards (towards the bottom area 15 or the cells adhered on it) and are in electrical contact with the environment. Due to full extension of the isolating material 5 in the region between each opposing arranged areas 9 of the coplanar electrodes 2, 3, 4, or at least in the area exposed to the liquid between the electrodes, where these show parallel lines, the electrical field can be focused or the current can be limited to the radius of action of interest. It is further a particular advantage that focusing of the electrical field in the region of the targeted cells or a limiting of the electrical current to the radius of action from now is possible by using of co-planar electrodes 2, 3, 4, which provide constant and more stable field strengths and current densities in the targeted region between the electrodes 2, 3, 4 and the bottom area 8. Suitable isolating materials therefore are for example plates or injected molding articles made of common, preferably thermoplastic synthetic materials, such as polyvinyl chloride, polystyrol, polypropylene, polyethylene or polycarbonate. By means of the arrangement according to the invention current leakage through the each opposing areas 9 of coplanar parts of the electrodes 2, 3, 4 can be avoided and thus voltage pulses of constant current are generated. Thus the arrangement according to the invention can be applied, for example per reaction depending on the area of the culture floor of cells to be treated, with one or more successive pulse discharges of low energy/currents to limit the necessary power per discharge.

For example an electrodes-isolator-sandwich can be used, in which the electrodes are poled alternating. In such an arrangement the field in the region below the active electrodes practically does not exist and therefore has no effect on cells located in the region below the active electrode. These regions are in close vicinity to an electrical conductor (the electrodes) and therefore outside of a considerable field. Active regions, i.e. regions having a sufficient electric field, are only those regions located between electrodes having opposite poles. In order to minimize the regions underneath the electrodes which are not exposed to an electric field, the electrodes may be designed, for example, as thin as possible (e.g. 50 µm) so that larger areas of the bottom area overgrown with cells are covered by the electrode arrangement with active regions of electrode/isolator combinations. However, reducing the thickness of the electrodes is often neither reasonable nor technically feasible so that the effect of such measure is limited.

Thus, according to the invention, after the first voltage pulse, at least one further electric field is generated in the space between the electrodes 2, 3, 4 and the bottom area 8 by at least one further voltage pulse. According to the invention at least one of the electrodes that has been active before is floating in this case so that the further and accordingly second electric field may act as well on the cells within the region underneath the electrode being passive now. Thus, if in the exemplary embodiment depicted in FIG. 1, for example, the electrode 3 in the middle would have been active during the first voltage pulse, i.e. connected either to voltage (+) or ground (−), this electrode 3 could be floating (passive) during the second voltage pulse, so that even the region underneath the electrode 3, which is simultaneously located between electrodes 2 and 4 being active during the second voltage pulse, can be exposed to a sufficient electric field. In this manner, the bottom area 8 may be exposed more uniformly and hence a higher number of cells may be effectively electrically treated.

Figure 2:
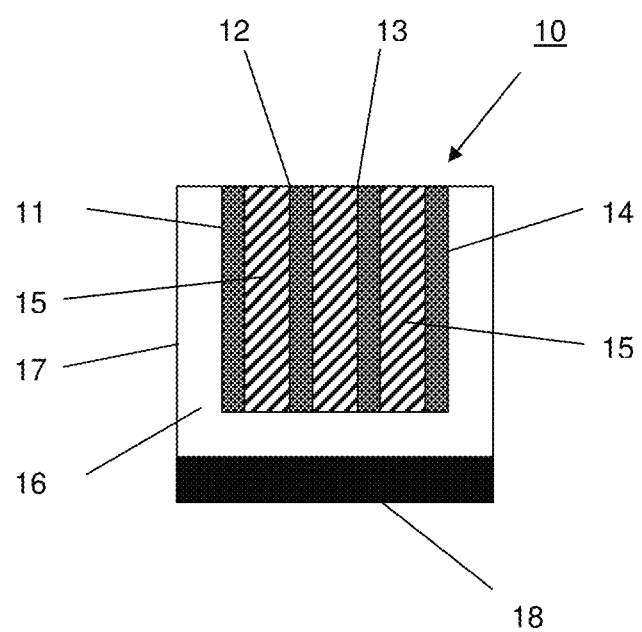
FIG. 2 shows a schematic side view of an alternative electrode arrangement of an exemplary device according to the invention having four electrodes.

FIG. 2 shows an alternative electrode arrangement 10 of an exemplary device according to the invention having four electrodes 11, 12, 13, 14. The electrode arrangement 10 substantially corresponds to the electrode arrangement 1 according to FIG. 1, but for the difference that it comprises four coplanar electrodes 11, 12, 13, 14 extending into the inner space 16 of a container 17. The container 17 also comprises a bottom area 18 on which living cells may adhere and grow (adherent cells). The space between electrodes 11, 12, 13, 14 is each completely filled with an electrically isolating material 15 so that no current can flow via the space located between electrodes 11, 12, 13, 14 if a voltage is applied to electrodes 11, 12, 13, 14. According to the invention, electrodes 11, 12, 13, 14 may be triggered, for example, such that electrodes 11 and 13 are active when a first voltage pulse is applied, while electrodes 12 and 14 are floating. During the following voltage pulse, electrodes 11 and 13 that have been active before are floating, while electrodes 12 and 14 are active. Due to this advantageous approach, the entire region between the outer electrodes 11 and 14, in particular also the region underneath each of the inner electrodes 12 and 13, is exposed to a sufficient electric field. As a result, the entire bottom area 18 and accordingly the cells adhering thereto are electrically treated uniformly (see also FIGS. 10 and 11).

Figure 3:
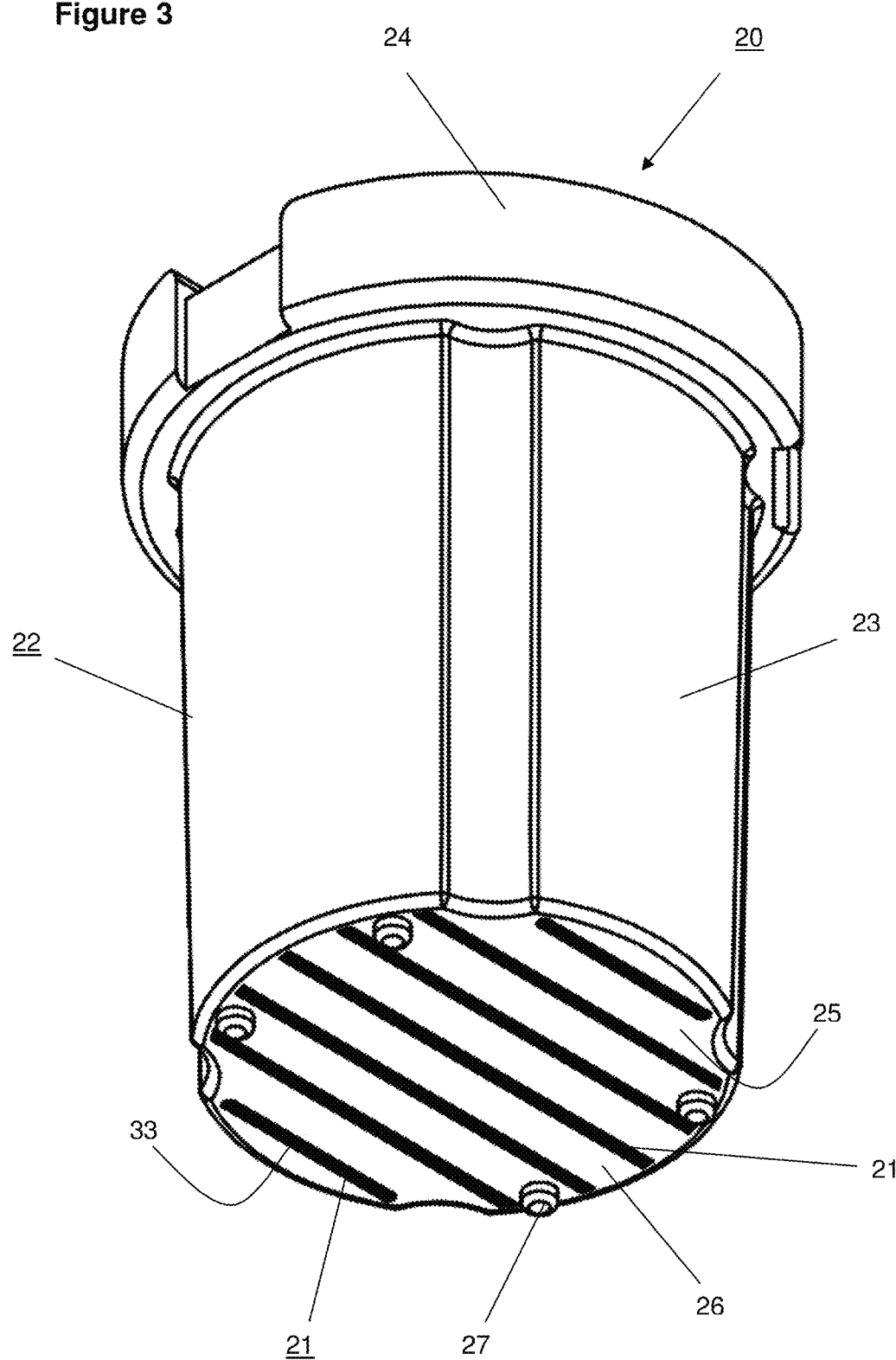
FIG. 3 shows a perspective view of the underside of an exemplary embodiment of an exemplary electrode arrangement for a device according to the invention.

FIG. 3 shows a schematic view of the underside of exemplary embodiment of an electrode arrangement 20 according to the invention. The electrode arrangement 20 comprises seven electrodes 21, which are described hereafter in detail referring to FIGS. 5 and 7. The electrodes 21 are arranged in a carrier 22, which essentially is formed cylindrical. The carrier 22 comprises a base body 23 and a border area 24 at the upper end of the base body 23, whereby the outer diameter of the border area 24 is larger than the outer diameter of the base body 23, thus the border area 24 protrude outward of the base body 23. The electrodes 21 are arranged to a large extent within the base body 23 and are exposed with their lower face surface 33 at the underside 25 of the carrier 22, thus they are in contact with the environment. The single electrodes 21 are each electrically separated from each other by an isolating material 26, whereby in this embodiment the space between the single electrodes 26 is completely filled with the isolating material 26. The isolating material 26 between the opposing areas of the electrodes 21 ensures that when applying a voltage on the electrodes no current is allowed to leak across the space between the electrodes 21, if the electrodes are dipped in the electrically conductive liquid. The isolating material rather causes that when applying a voltage on the electrodes 21 current is passing through the face surface 33 of electrodes 21 and an electrical field is generated below the underside 25 of carrier 22. Because no significant current leaks across the space between the electrodes 21 voltage drop during discharge of a capacitor or another non-permanent voltage source takes longer, thus over time constant and more stable currents passing, which generate for most of the biological methods, for example transfection, a sufficiently strong electrical field over the period of discharge. The electrode arrangement 20 in particular is provided for insertion into a container at least partially filled with liquid, for example reaction vessel, a cell culture tray or a "well" of a multi-well-plate, whereby said container provides a bottom area, on which living cells are allowed to adhere. The adherent cells on the bottom area of the container are usually covered with a suitable liquid, for example a cell culture medium or a solution adapted to the desired electrical treatment, whereby the electrode arrangement 20 displaces at least a part of said liquid during insertion in the container. Thus the electrodes 21 with their face surfaces 33 are not lying directly on the bottom area of the container and thus not on the cells, the underside 25 of the carrier 22 provides four spacer 27, which ensure a sufficient distance between the electrodes 21 and the bottom area of the container. By adjusting the distance to an empirically determined value, efficiency of the method according to the invention can be optimized (see FIGS. 7 and 8).

Figure 4:
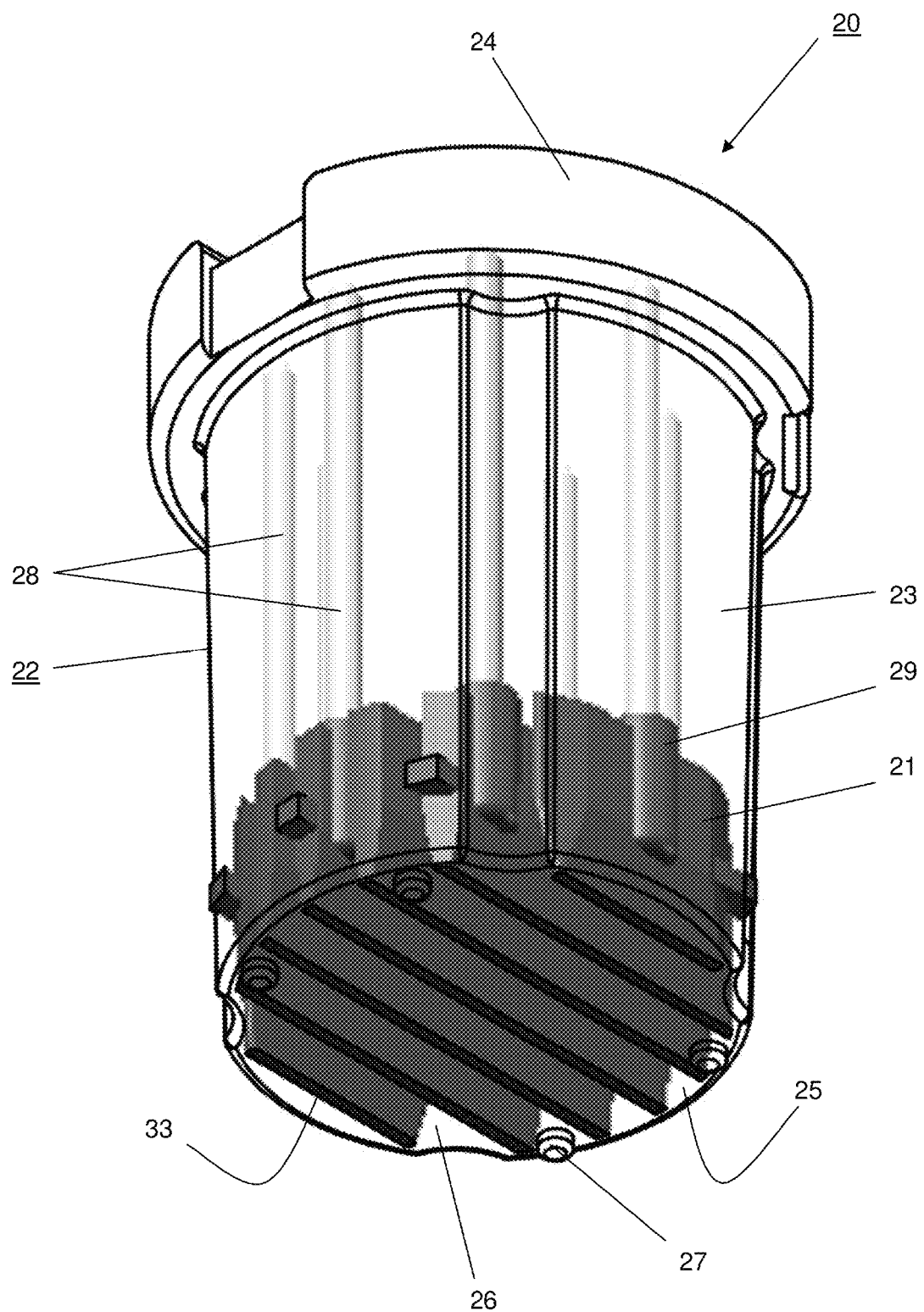
FIG. 4 shows a further perspective view of the electrode arrangement according to FIG. 3, whereby in this illustration the inner parts of the electrodes and contact elements are visible.

FIG. 4 shows a perspective view of the electrode arrangement 20 according to FIG. 3, whereby the internal parts of the electrode 21 are visibly shown in this depiction. It is clear form this depiction that the electrodes 21 in particular are formed plate-shaped, whereby the thickness of the electrode plates decreases towards the underside 25 of carrier 22. The exposed face surfaces 33 of the electrodes 21, which are in contact with the liquid in the container, are thus essentially thinner as the parts of the electrodes 21 placed within the base body 23. The advantage thereof is that the region below of each electrode 21 is minimized, within an effective electrical treatment of cells is not possible because of the too weak electrical field. In contrast at the opposing end, the electrodes 21 have to exhibit an increased thickness because these have to be efficiently contacted here for establishing a sufficient electrical contact. The electrical contact to each of the used voltage source is established in case of the present embodiment by pin-shaped contact elements 28, which are inserted into thicken areas 29 of the electrodes 21. The contact elements 28 are linked electrically with a voltage source each at its ends opposing to area 29 by means of a suitable contact device. The voltage source for example might be one or more capacitors, which allow controlled release of voltage pulses. The generated voltage pulses are forwarded to the electrodes 21 across the contact elements 28, thus at the underside of the electrodes 21, that means below the underside 25 of carrier 22, an electrical field is established, which because of the isolating material 26 between the electrodes is limited or focused on the space between the cells and the cell facing side of electrodes 21.

The electrode arrangement 20 according to the invention is manufactured preferably by an injection moulding process. Thereby first the contact elements 28 are inserted into a suitable injection moulding tool and then encapsulated with an electrically isolating polymer. In a second step then an electrically conductive polymer is injected, which form the electrodes 21. Alternatively the electrodes can be made of metal, preferably aluminum. In this embodiment first the metal electrodes are inserted into the injection moulding tool and then encapsulated with an electrically isolating polymer. In this embodiment the metal electrodes provide preferably upwards outstanding appendixes, which are suitable for contacting the electrodes electrically.

Figure 5:
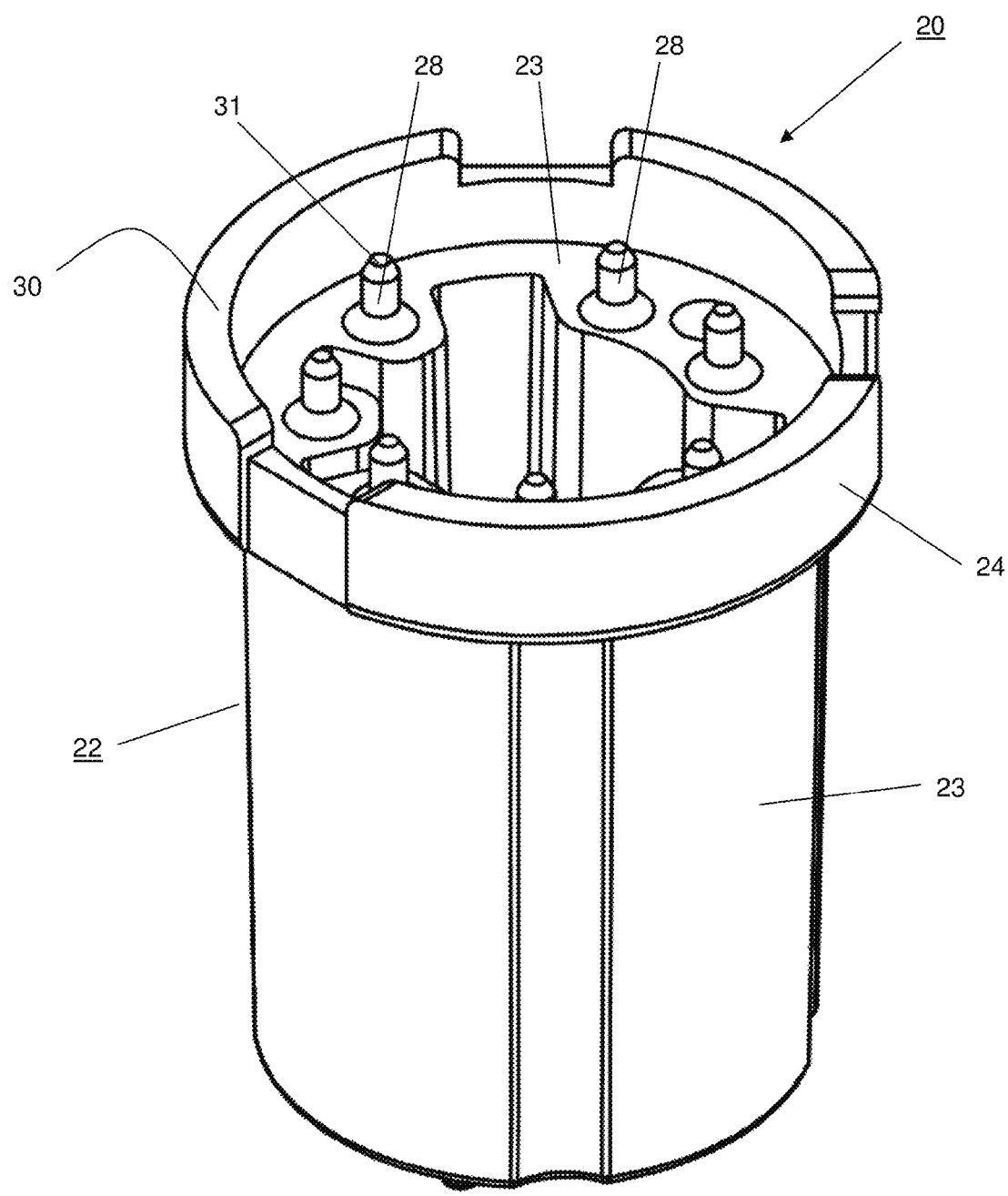
FIG. 5 shows a perspective view of the upper side of the electrode arrangement according to FIG. 3.

FIG. 5 shows a perspective view of the upper side 30 of the electrode arrangement 20 according to the invention relating to FIG. 3. It is clear thereof, that the contact elements 28 are outstanding upwards from the base body 23. Thus the contact elements 28 are completely surrounded with the electrically isolating material of the base body with the exception of the exposed ends 31. Using these exposed ends 31 the contact elements 28 can be electrically contacted by means of a suitable device to a voltage source.

Figure 6:
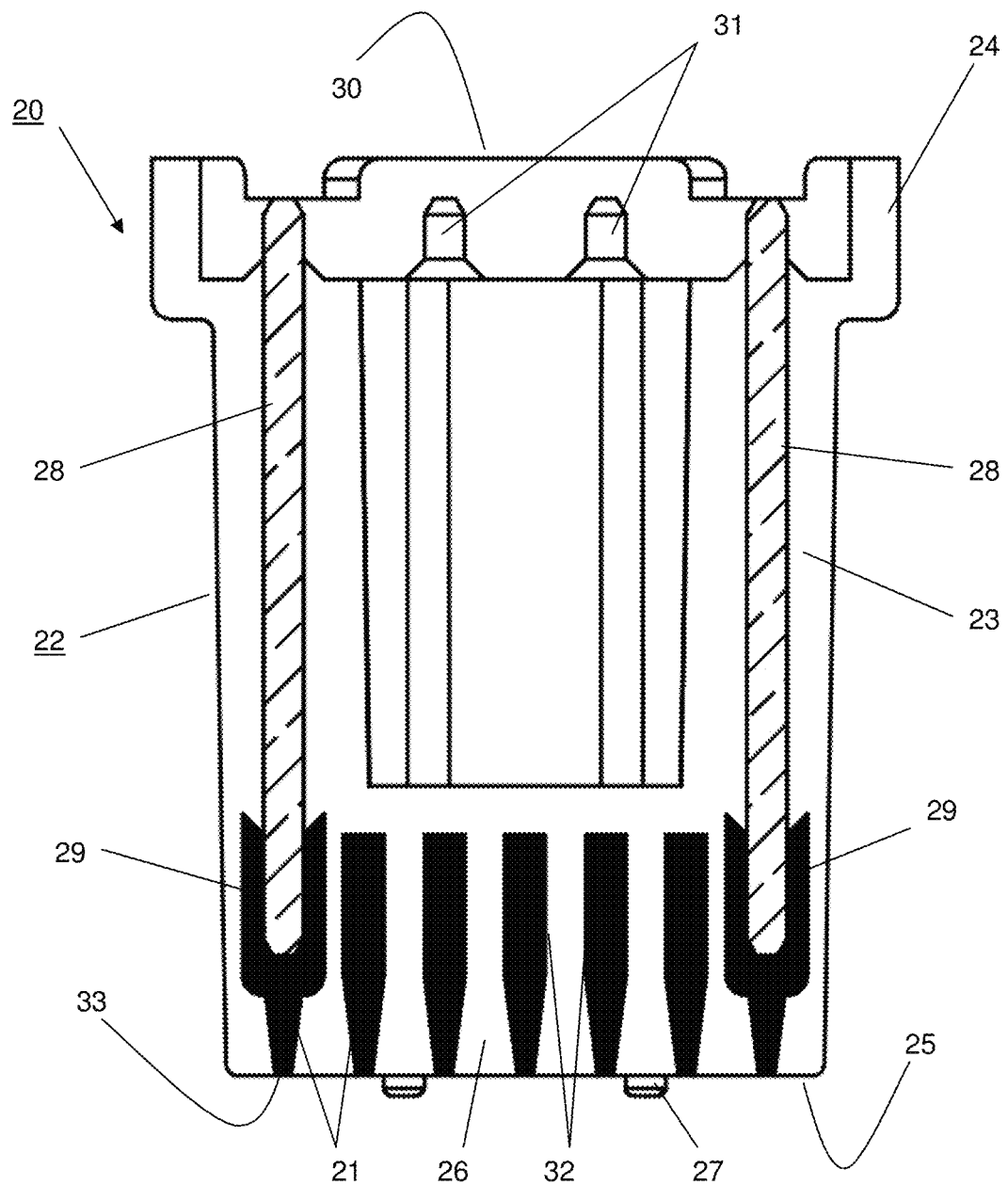
FIG. 6 shows a longitudinal section through the electrode arrangement according to FIGS. 3 to 5.

FIG. 6 shows a longitudinal section across the electrode arrangement 20 relating to FIGS. 3 to 5. From this depiction it is clear, that the diameter of the electrodes 21 tapers towards the underside 25 of the base body 23, thus the area below the electrodes 21, within the insufficient electrical field establishes, is minimized. At the opposing end of the electrodes 21 there is the area 29 with the increased thickness, in which contact elements 28 are inserted or injected respectively. This particular advantageous embodiment ensure a sufficient electrical contact between the contact elements 28 and the electrodes 21, thus an effective forwarding of voltage pulses from the voltage source until the electrodes 21 is ensured. If the electrode arrangement 20 is inserted into a container filled with liquid, on which bottom area living cells are adhered, the spacer 27 make sure, that the optimal distance between the underside of the electrodes 21 and the cells to be treated is set. Because the space between the each opposing arranged areas 32 of the electrodes 21 are completely filled with the isolating material 26, no liquid gets between the areas 32 of the electrodes 21, thus no current is allowed to leak through the region between the areas 32 of electrodes 21. In this way via application a voltage on the electrodes 21 the electrical field is concentrated at the cell facing side of the electrodes and limited or focused on the space between the cells and the electrodes 21. In this way cells can be treated very effectively and with relatively low demand of power. A further advantage of the invention is, that the electrode arrangement 20 displaces a part of the liquid during insertion into the container, because there are no intermediary spaces between the electrodes 21. Because of this reason the container have to be filled only with a small liquid amount, whereby solutions and substances necessary for the treatment can be saved and thus costs can be reduced.

Figure 7:
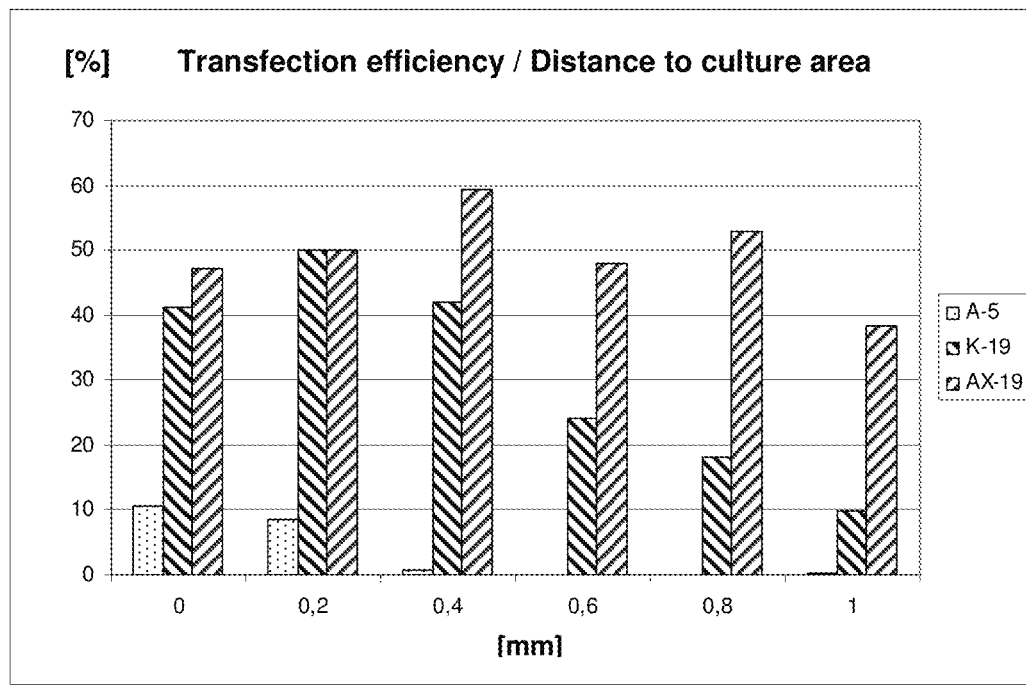
FIG. 7 shows in a bar diagram of the transfection efficiency as a function of the distance between the electrodes in an electrode arrangement according to the invention and the cells adhered on the culture area at three different high voltage pulses (x-axis: distance [mm], y-axis: transfection efficiency [%], A-5=weak voltage pulse, K-19=moderate voltage pulse, AX-19=high voltage pulse).

FIG. 7 shows the dependency of transfection efficiency on the distance of the electrodes between the cells to be treated with varying magnitude of voltage pulses respectively. Transfection means in this context the introduction of nucleic acid molecules (here DNA) into living cells by means of electrical voltage pulses. While at relatively high voltage (AX-19) there is an only poor dependency of the transfection efficiency on the distance between the electrodes and the cells, at low voltage (A-5) it is seen, that the transfection efficiency increases with decreasing distance between the electrodes and the cells. In contrast moderate voltage pulses (K-19) show an optimum at medium sized distances. It illustrates that the distance between the electrodes and the cells has a more or less great influence on the transfection efficiency depending on the strength of the voltage pulse. Therefore, in order to optimize transfection efficiency, the distance is adjusted to an empirically determined value according to the invention, e.g. by respectively sizing the spacer 27 of the electrode arrangement 20 according to FIGS. 3 to 6.

Figure 8:
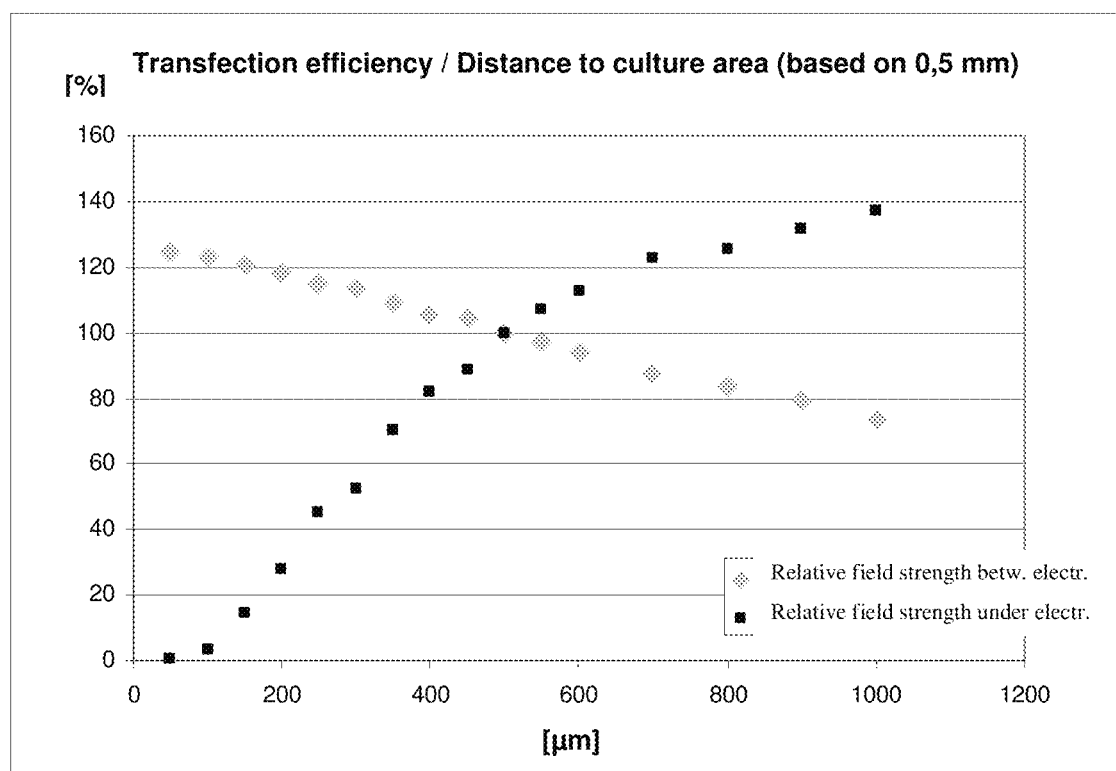
FIG. 8 shows a diagram of the relative electric field strength as a function of the distance of the electrodes to the bottom of the container based on the field strength at a distance of 500 µm (x-axis: distance [µm], y-axis: relative transfection efficiency [%]). Here, the relative field strength between active electrodes (gray diamonds) and the relative field strength underneath the floating (passive) electrodes (black squares) are depicted.

FIG. 8 shows the relative electric field strengths within the region between the electrodes and the bottom of a container as a function of the distance of the electrodes to the bottom of the container. Thereby, the field strength is respectively based on the field strength at a distance of 500 µm, i.e. the field strength of both graphs was set to 100% for this distance. The field strengths between the active electrodes and underneath the passive electrodes act contrarily, i.e. while the field strength between the active electrodes increases if distances decrease, the field strength underneath the passive electrodes almost reaches zero. The field strength between the active electrodes decreases if distances increase, while the field strength underneath the passive electrodes increases further. At large, the field strength between the active electrodes decreases if the distance increases, while the field strength underneath the floating electrodes reaches a maximum value at a medium distance, thus decreases based on this maximum value if distances decrease or increase. According to the invention, the distances of the electrodes to the cells are therefore adjusted as a function of the conditions of the process such that the field strength underneath the floating electrodes is close to the maximum value and also reaches a value as high as possible between the active electrodes.

Figure 9:
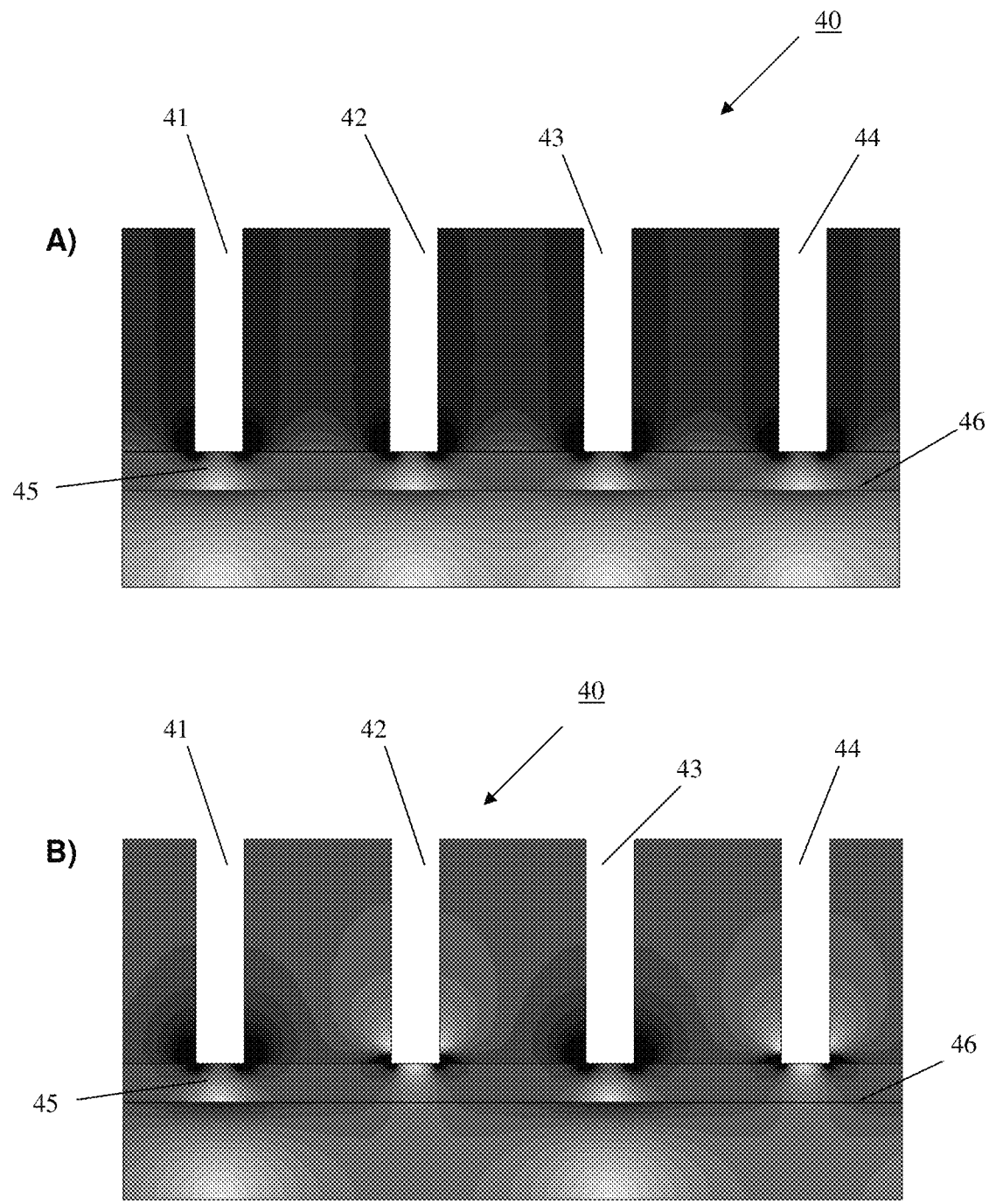
FIG. 9 shows simulations of electric fields in a cell culture container with active electrodes only (A) as well as with active and floating electrodes (B).

FIG. 9 shows a simulation of electric fields in a cell culture vessel at exclusively active electrodes (top) as well as at active and floating electrodes (bottom). While common methods and devices for generation of electric fields have the disadvantage, that the electric field orthogonal below the active electrodes is minimal and therefore electrical treatment of cells in this region is insufficient, it becomes clear, that due to including of floating (passive) electrodes to the method according to the invention a more uniform and thus more efficient treatment of cells is allowed. The herein showed exemplary electrode arrangement 40 comprises four electrodes 41, 42, 43, 44, which generate an electric field by means of applying a voltage in the space 45 between the electrodes 41, 42, 43, 44 and the bottom area 46 of a cell culture vessel. The strength of the electric field is simulated in this depiction by the density of the field lines. Thereby darker regions indicate a higher field strength and brighter regions a lower field strength. In illustration A) all electrodes 41, 42, 43, 44 are active. In this case the field strength is high merely between the electrodes 41, 42, 43, 44 and at their exposed ends (dark regions). In contrast the field strength in space 45 in the regions below the electrodes 41, 42, 43, 44 is low, thus cells to be treated on the bottom area 46 are exposed merely irregular to a sufficient field electric field. Therefore according to the invention, as shown in illustration B, in this embodiment first voltage is applied only to the both electrodes 41 and 43, while the other two electrodes 42 and 44 are floating (passive). This results in, that in regions below the passive electrodes 42 and 44 a stronger, merely slight due to the passive electrodes 42 and 44 weakened electric field have an effect on the cells adhered on the bottom area 46. If now a voltage pulse is applied to the previously passive electrodes 42 and 44 and previously active electrodes 41 and 43 are floating, a stronger electric field affects in the region below the electrodes 41 and 43 as well. Therefore cells adhering on the bottom area 46 are allowed to be uniformly treated with a sufficient electrical field by means of the method according to the invention.

Figure 10:
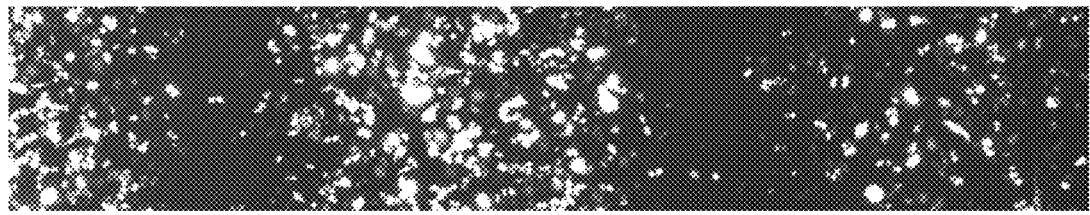
FIG. 10 shows fluorescence micrographs of cells transfected with a plasmid (electroporation using the Nucleofector®, Lonza) coding for the fluorescing protein MAXGFP® (Lonza). Top: A) All electrodes were active during electrotransfection. Middle: B) Same conditions as above, but only half of the electrodes was active during transfection while the other half was floating. Bottom: C) The same cells have been exposed to a second electric field (voltage pulse) again but active and passive electrodes were interchanged at the second pulse, i.e. all electrodes that have been active at the first pulse were floating at the second pulse while the electrodes that have been passive before were active at the second pulse.
Figure 10:
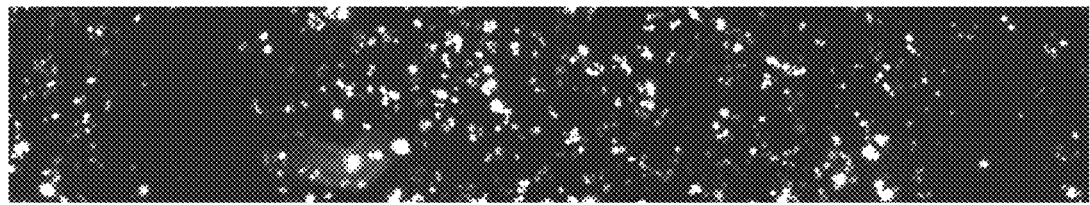
Figure 10:
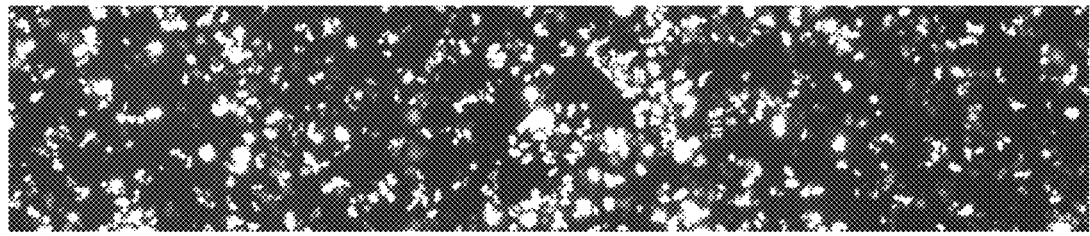

FIG. 10 shows microscopic images of fluorescently marked cells, which were transfected according to the prior art (A) and by means of the method according to the invention (B and C). In electrotransfection of the cells of depicted in illustration A) all electrodes were active, that means all electrodes were either connected with high voltage or ground. The cells successfully transfected with the plasmid are fluorescent and thus clearly to identify. Illustration A shows gaps ("shadows") within the lawn of transfected cells, which correspond to the regions below the active electrodes. In this regions the electric field was not strong enough to transfect the cells successfully. In electrotransfection of cells shown in illustration B) only the half of the electrodes was active, while the other half was floating. In comparison to transfection according to illustration A), in this case in total less cells have been transfected successfully but there are less gaps present as well or the distance between the regions of very low transfection efficiency are larger. The transfection efficiency is decreased here initially, because the electric field across the entire culture area at total is weaker due to the increased distances between the active electrodes. According to the inventive method the same cells then were exposed again with a second electric field (voltage pulse), whereby during said second pulse active and passive electrodes were reverse that means all during first pulse active electrodes were floating during the second pulse, while the previously passive electrodes were active during second pulse. Now, no more gaps are detectable, that means all regions, including the regions below the electrodes show a high transfection rate (illustration C). The method according to the invention thus allows an across the entire culture area very uniformly and humongous treatment of cells. In particular the comparison of illustration A) (prior art) and C) (method according to invention) demonstrates the significant advantages of the method according to the invention against to the common methods.

Figure 11:
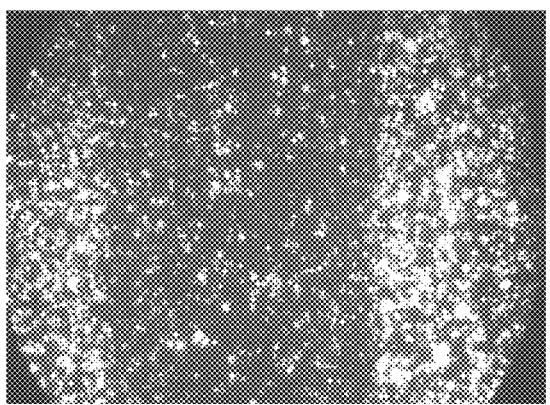
FIG. 11 shows fluorescence micrographs of cells transfected with a plasmid coding for the fluorescing protein MAXGFP® (Lonza) using the method according to the invention (electroporation using the Nucleofector®, Lonza). Top: A) time gap between two voltage pulses <0.5 s. Bottom: B) time gap between two voltage pulses 2.0 s.
Figure 11:
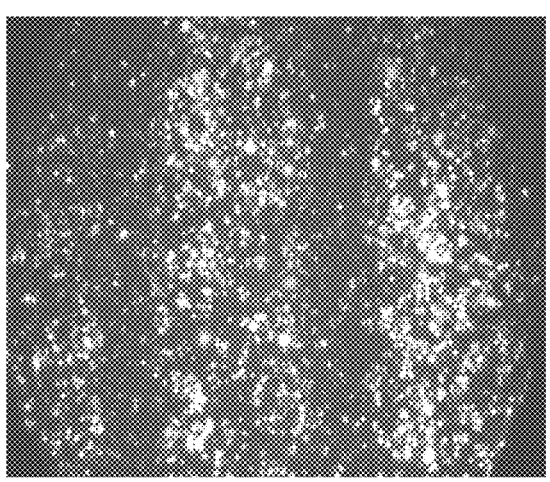

FIG. 11 shows microscopic images of fluorescent cells, which were transfected by means of the method according to the invention, whereby the distance between the two voltage pulses were varied. At very small distances (A: <0.5 seconds) an undesired contamination of transfection efficiency occur. This effect is neutralized with increasing distances between the voltage pulses (B: 2.0 seconds). In order not to prolong the whole processing unnecessarily, the distances should be optimized, that means adapted to process conditions or electrical parameter, sample volume, buffer solution or culture medium, temperature and/or cell type. Preferably the time lag between two voltage pulses is used to expose first multiple samples one after another to the first voltage pulse and then these samples one after another to the second voltage pulse. Due to these particularly advantageous time-interleaving of voltage pulses is allowed to be minimized the process duration in case of treatment of multiple samples.

Figure 12:
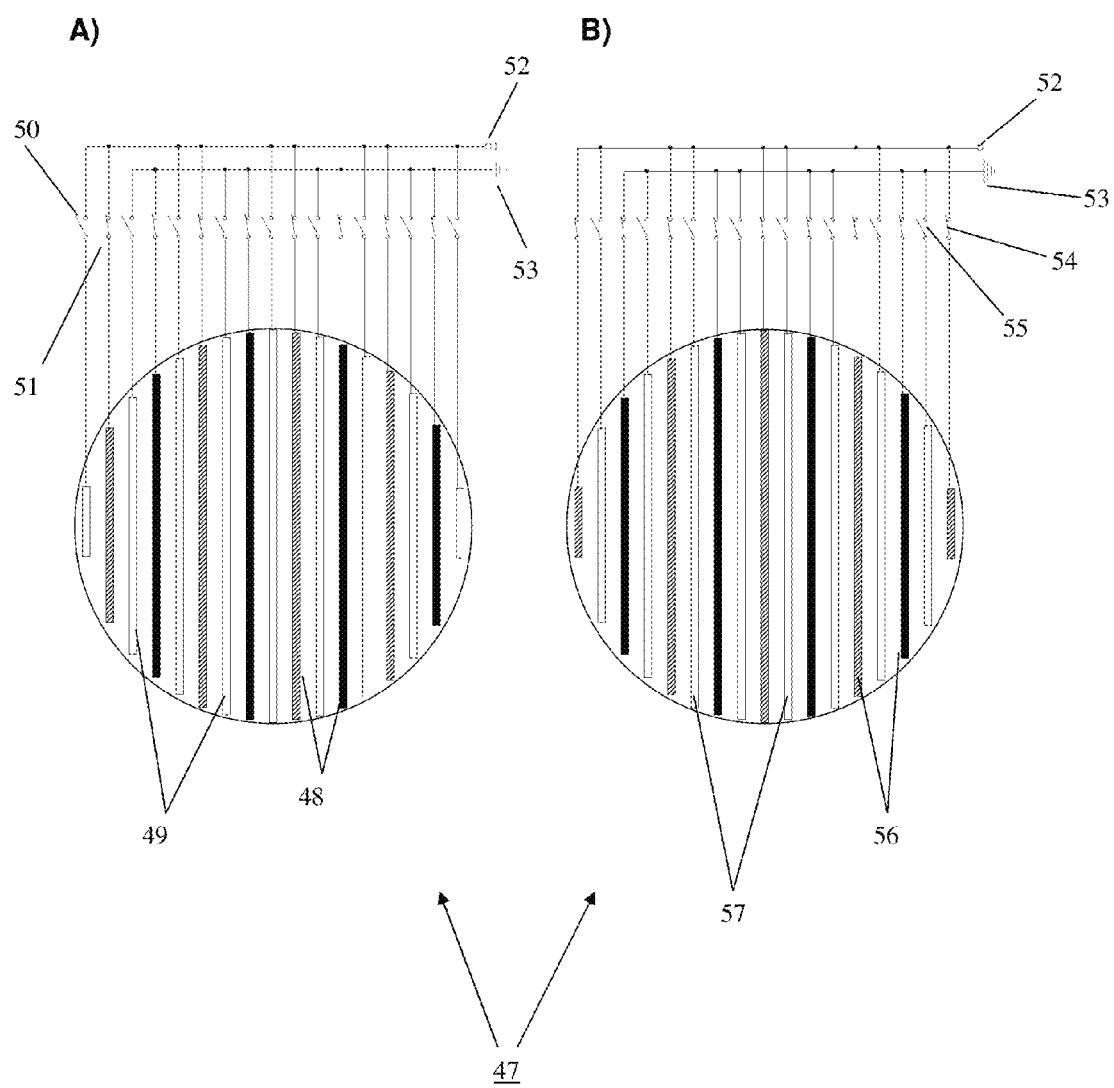
FIG. 12 shows schematic representations of the electric interconnection of an electrode arrangement having 17 electrodes, wherein in the representation depicted at the right side (B) the electrodes that are active electrodes in the representation depicted at the left side (A) are floating (passive). Transparent electrodes: floating (passive). Dashed electrodes: active (high voltage). Black electrodes: active (ground).
Figure 13:
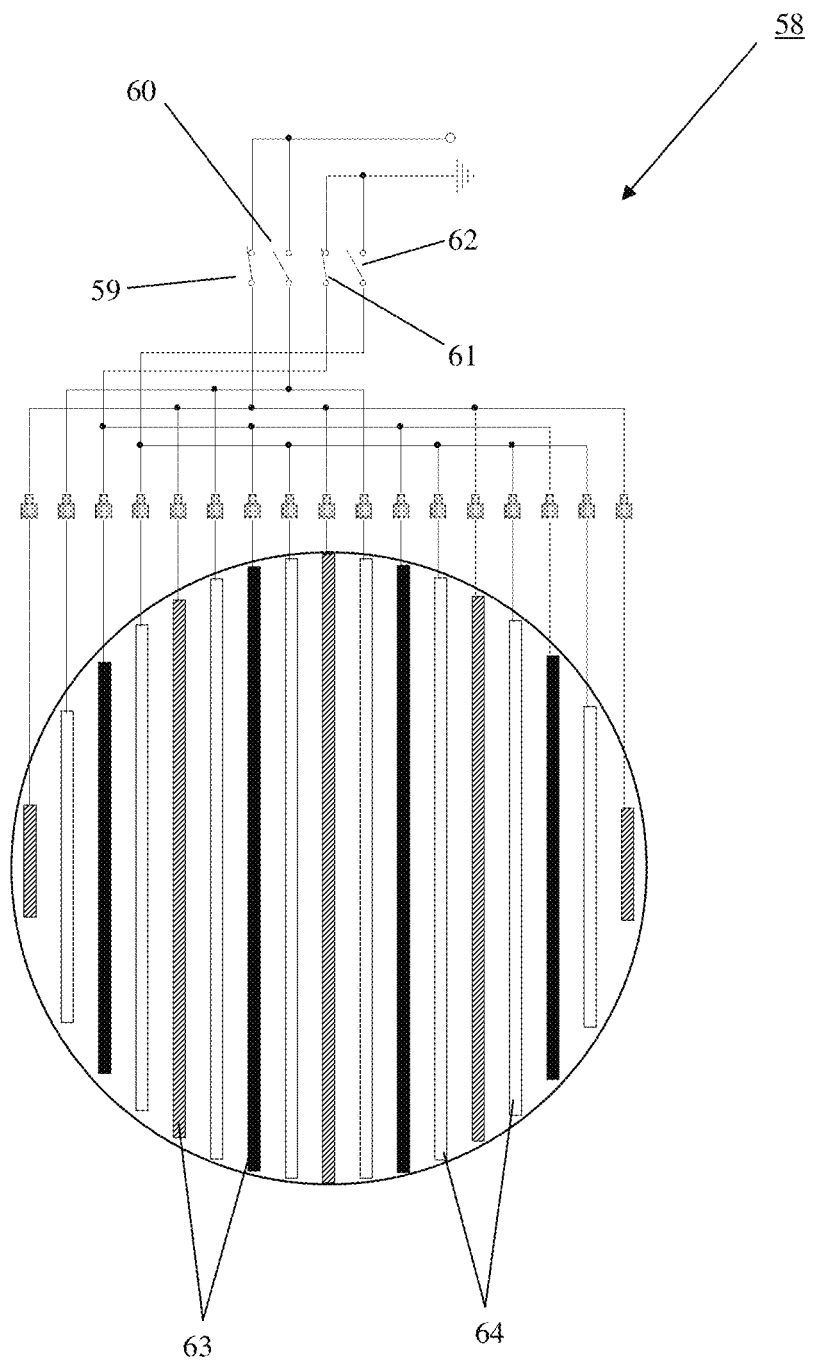
FIG. 13 shows a schematic representation of the electric interconnection of the electrodes of an exemplary device according to the invention having four switching. Transparent electrodes: floating (passive). Dashed electrodes: active (high voltage). Black electrodes: active (ground).

For carrying out the method according to the invention the electrodes have to be triggered either individual, as shown in FIG. 12, or in groups, as shown in FIG. 13. This is done preferably by switching devices, for example IGBTs, MOS-FETs or relays, which can be in an open or closed state. At open state the switching devices do not supply current, thus the connected electrodes are electrically isolated and therefore floating. At closed state the switching devices supply electrical current, thus current is allowed to pass the connected electrodes. The electrodes have an electric potential (plus or minus) and acts as anode or cathode. They are indicated as active electrodes.

FIG. 12 shows a switching device 47 for carrying the method of the invention with seventeen electrodes 48, 49, 56, 57. The coplanar arranged electrodes 48, 49, 56, 57 are each connected via a switching devices 50, 51, 54, 55 either with a voltage source 52 or ground 53. Illustration A) shows the state of switching device 47 during establishment of the first electric field. The part of electrodes 48, 49 which are connected with the open switching devices 50 are first floating electrodes 49 in this case. The part of electrodes 48, 49 which are connected with the closed switching devices 51 are active electrodes 48 which finally generate the first electric field for treatment of the cells. The electric field orthogonal below the active electrodes 48 is minimal, thus the cells are not sufficiently treated in this region. Illustration B) shows the state of switching device 47 during establishment of the second electric field. The switching device 47, which were open during establishment of the first electric field, are closed in this case, while the switching devices 55, which were closed during establishment of the first electric field, are open now. The consequence is that the electrodes 45 which were floating during the first electric field, are the active electrodes, which generate the second electric field, during establishment of the second electric field. The electrodes 57, which were active during establishment of the first electric field, are floating during establishment of the second electric field. Because during establishment of the first electric field all active electrodes 56 are arranged between two floating electrodes 57, the regions below the active electrodes 56 are exposed to the second electric field which is generated by the active electrodes 56. Therefore by the second electric field the cells, which were not sufficiently treated during the first electric field, are treated electrically as well, thus in total all cells are treated uniformly.

FIG. 13 shows an exemplary device 58 according to the invention for carrying out the method according to the invention with four switching devices 59, 60, 61, 62. The switching devices 59 and 60 are connected with a voltage source, whereas the switching devices 61 and 62 are connected to ground. The electrodes (active electrodes 63: dashed or black, floating electrode 64: transparent) of device 58 are divided in two groups, whereby one group is electrically linked to switching devices 59 and 61 and the other group with the switching devices 60 and 62. In the herein shown embodiment thus seventeen electrodes 63, 64 are connected with a voltage source via merely four switching devices 59, 60, 61, 62. In the herein shown state the active electrodes 63 (first group) are connected via closed switching devices 59 and 61 with a voltage source or ground, thus in case of applying a voltage to the active electrodes 63 a first electric filed between the active electrodes results. Because the switching devices 60 and 62 are open, the hereby linked electrodes 64 (second group) remain floating or passive in this state. In order to provide a sufficient treatment to the cells in the region below the active electrodes 63, which were exposed only to a minimal electric field in the described state, for establishment of the second electric field the switching devices 59 and 61 are opened and the switching devices 60 and 62 are closed in according to the invention. Due to this simply switching the electrodes of the first group, which were active electrodes 63 in the described state becomes floating electrodes, whereas the electrodes of the second group, which were floating electrodes 64 in the described state becomes active and generate a second electric field. This second electric field ensures, that the region below the electrodes of the first group 63 is also applied with a sufficient treatment, thus in total a uniform and efficient treatment of the cells is ensured. The device 58 according to the invention implies the advantage, that it functions with four switching devices and due to switching of the switching devices can switch fast between the electrodes of both groups. Each group of electrodes can be switched either active or passive, whereby all electrodes of one group are switched equal at the same time. (active or floating). Because of this constellation of the electrodes 63, 64 the device 58 according to the invention has, for example in comparison to the switching device 47 of FIG. 12, a significant smaller amount of switching devices, which reduces the needed equipment and the susceptibility of the device 58.

Figure 14:
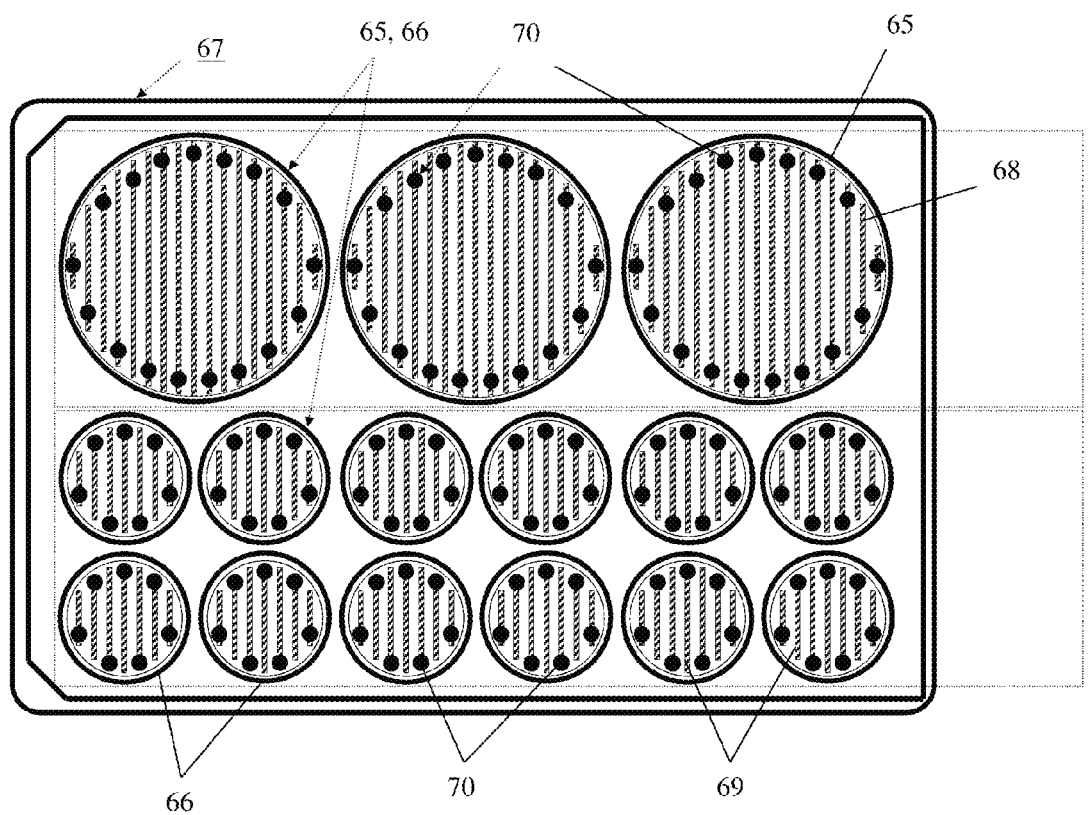
FIG. 14 shows a top view of schematic representations of electrode arrangements with contact points. The electrode arrangements have different dimensions for cell culture plates having 3 larger reaction spaces ("6-well" size) and 12 smaller reaction spaces ("24-well" size).

FIG. 14 shows schematic depictions of electrodes arrangements 65, 66 with different dimensions for cell culture plates with 3 bigger culture wells ("6-well" size, electrode arrangement 65) and 12 smaller culture wells ("24-well" size, electrode arrangement 66). In order to save material and to reductive constructive effort, according to the invention joint contact points for the electrodes arrangements at different sizes are chosen. Hereby it is allowed advantageous to reduce significantly the contact elements, which are necessary relating to device for the electrical contacting of the electrodes. The shown reception area 67 of the cell culture plate has a section of three greater culture wells and a section for twelve smaller culture wells. The greater culture wells are equipped for electric treatment of therein placed cells with appropriate sized electrodes arrangements 65, for example in form of dipping electrodes, which each comprises seventeen electrodes 68. The smaller culture wells are quipped for electric treatment of therein placed cells with appropriate sized electrodes arrangements 66, for example with dipping electrodes, which each comprise seven electrodes 69. The electrodes arrangement may be for example be integrated in a cover of the cell culture plate or be fixed at a carrier unit of the corresponding contacting device. Such a contacting device comprises contact elements as well, which are arranged in each section of the reception area, as explained below, correspondingly to the contact points of the electrodes. To each electrode 68, 69 a contact point 70 respectively is assigned, to which the each electrode 68, 69 is allowed to be contacted by means of a contact element, thus an electrical contact to a voltage source, for example capacitor, can be established. A device for contacting such a "mixed" cell culture plate 67 thus needs 3×17+12+7=135 contact elements. A device for contacting of two different formats of cell culture plates, for example "6-well" size (6 culture spaces for electrodes arrangements with 17 electrodes respectively) and "24-well" size (24 culture spaces with 7 electrodes respectively), would even need 6×17+24×7=270 contact elements.

Because for manufacturing of a sufficient electric contact, by e.g. spring applied contact elements, a certain contact pressure is necessary, which compensates manufacturing tolerances as well, the amount of contact points or corresponding contact elements should be as low as possible. Thus the contact pressure force of a standard spring is approximately 0.4 N, which in turn in case of 270 contact elements could result a mechanical force of approximately 108 N (appr. 10 Kg). Thus it is desirable to minimize the amount of contact elements for reducing the technical and device relating effort.

Figure 15:
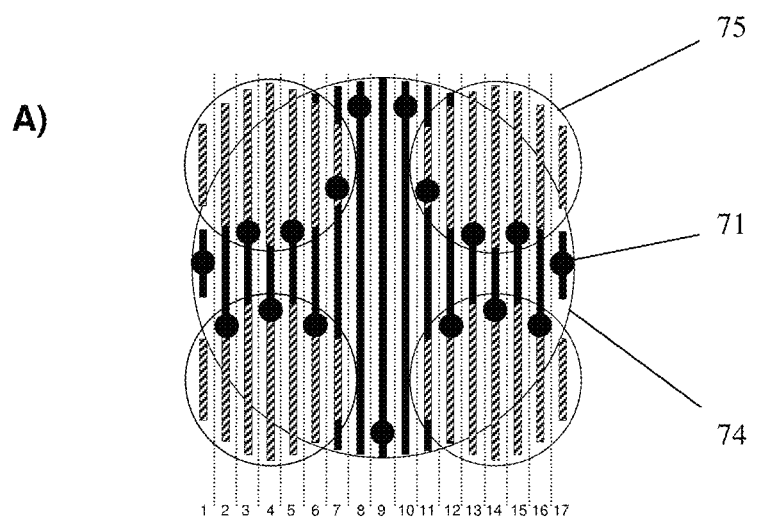
FIG. 15 shows a top view of schematic representations of electrode arrangements with contact points. Reference numbers 1 to 17 below the electrode arrangements respectively refer to the lines of the electrode pattern within which the electrode are respectively arranged. A) An exemplary and preferred arrangement of contact points for electrode arrangements having different dimensions for cell culture plates including at least one larger reaction space and at least four smaller reaction spaces. B) A further exemplary and preferred arrangement of contact points for electrode arrangements having different dimensions for cell culture plates including at least one larger reaction space and at least four smaller reaction spaces, wherein the arrangement of contact points and accordingly contact elements is optimized in respect of the manufacturing process.
Figure 15:
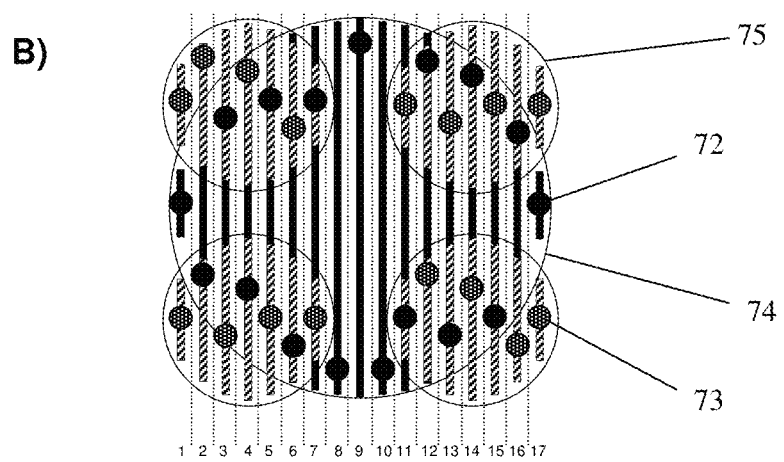

FIG. 15 shows exemplary and preferred arrangements of contact points 71, 72, 73 for electrode arrangements 74, 75 with different dimensions for cell culture plates with at least one greater reaction wells. (electrode arrangement 74) and at least four smaller reaction wells (electrode arrangements 75). The most contact points 71, 72, 73 can be arranged according to the invention, that they are identical for the various formats, thus can serve as contact points for both electrodes of grater electrodes arrangements 74 and for electrodes of smaller electrodes arrangements 75. In the herein exemplary presented formats only the medium electrodes (grid-Nos. 8-10) and the outer electrodes (grid-Nos. 1 and 17) of the greater electrodes arrangements 74 have a position respectively, which are not possible to bring into conformity with the corresponding positions of electrodes of the smaller electrodes arrangement 75. The remaining contact points (grid-Nos. 2-7 and 11-16) each are allowed to be used as contact points for corresponding electrodes of electrodes arrangements of both formats (illustration A). For each of herewith not recognized electrodes of the smaller electrode arrangement 75 then own contact points have to be assigned. An arrangement of contact points 72, 73 according to the invention, which is optimize regarding the production process as well, is shown in illustration B). The seventeen black contact points 72 represents points at which all electrodes of the greater electrode arrangement 74 (e.g. "6-well" size") and some electrodes of the smaller electrodes arrangements 75 (e.g. "24-well size") are allowed to be contacted. The sixteen hatched contact points 73 represents points at which exclusively the remaining electrodes of the smaller electrode arrangement 75 are allowed to be contacted. At total an adequate device for contacting both formats with a corresponding arrangement of contact elements have 6×(17+16)=198 contact elements within a reception area of cell culture plates. That is in comparison to the example shown in FIG. 14 (270 contact elements) a significantly reduced amount of contact elements, which reduces considerably the device relating effort.

Figure 16:
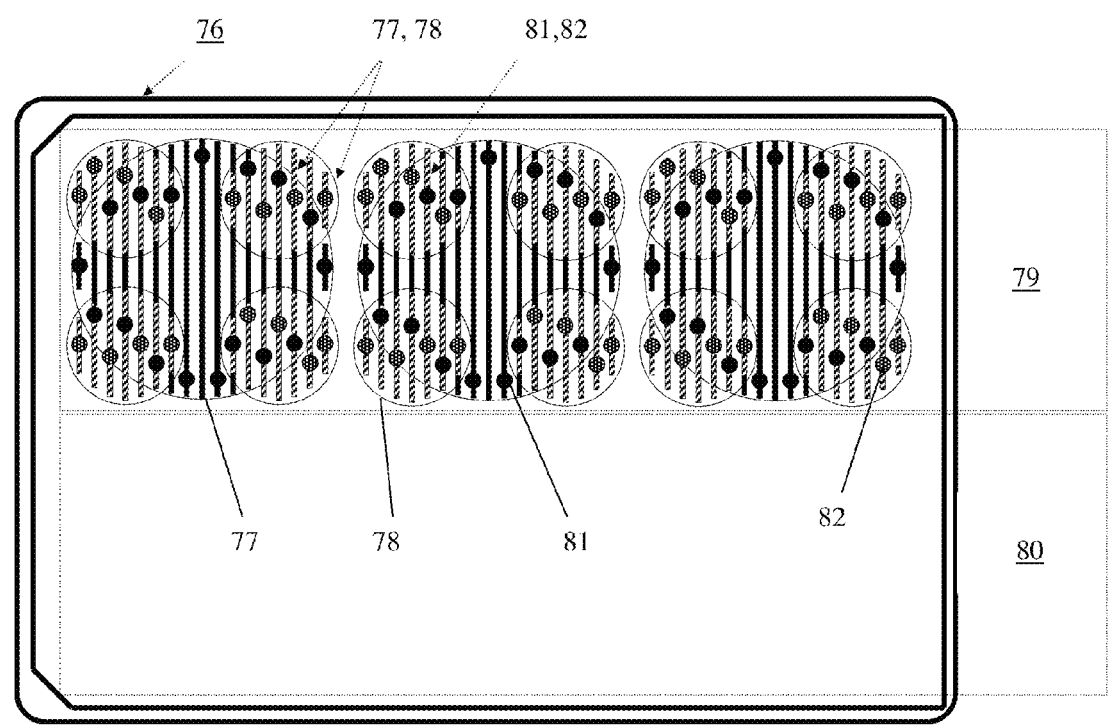
FIG. 16 shows a top view of schematic representations of a further exemplary and preferred arrangement of contact points for electrode arrangements having different dimensions for cell culture plates including 3 larger reaction spaces ("6-well" size) and 12 smaller reaction spaces ("24-well" size), wherein the contact elements can be rotated around an axis.

FIG. 16 shows another exemplary and preferred arrangement of contact points for electrode arrangements having different dimensions for cell culture plates having 3 larger reaction spaces ("6-well" size) and 12 smaller reaction spaces ("24-well" size). In this particularly advantageous embodiment, the electrodes and/or the corresponding contact elements for contacting the contact points are pivotable around an axis, preferably an axis disposed perpendicular to the plane of the cell culture plate. Hereby, the number of contact elements necessary on the part of the device can be further reduced to 3×(17+16)=99 contact elements in an advantageous manner. Moreover, this embodiment allows for additional treatment of cell culture plates having other dimensions, for example, "12- and 48-well" size. In the embodiment shown here, a reception area 76 for cell culture plates is provided, which, for example, may be part of a device for contacting electrode arrangements 77, 78. This device has contact elements not shown here, which may make electric contact with the electrodes of the electrode arrangement 77, 78. The reception area 76 comprises two sections 79, 80, within which contact elements are respectively provided in an arrangement corresponding to the contact points 81, 82 of the electrode arrangement 77, 78. The black contact points 81 represent positions, at which all electrodes of the larger electrode arrangements 77 ("6-well" size") and some electrodes of the smaller electrode arrangements 78 ("24-well size") may be contacted. The dashed contact points 82 represent positions, at which only the remaining electrodes of the smaller electrode arrangements 78 may be contacted. The first section 79 of the reception area 76 is provided for electrode arrangements 77, 78 and accordingly cell culture spaces ("wells") that are correspondingly dimensioned, wherein in this embodiment larger electrode arrangements 77 ("6-well" size) and smaller electrode arrangements 78 ("24-well" size) can be contacted electrically. Consequently, if a cell culture plate having 6 or 24 culture spaces or a mixed plate having 3 larger and 12 smaller culture spaces is placed in the reception area 76, in the first instance a half of the respective electrode arrangements can be electrically contacted in the first section 79. After treatment of the cells in the culture spaces, the plate is turned horizontally by 180° so that the other half of the culture spaces is placed in the first section 79 and can be electrically contacted. Alternatively, the unit including the contact elements may be turned instead of the plate so as to treat the respective other half of the plate. The second section 80 of the reception area 76 is either free and left unused or provided for the electrode arrangements and accordingly correspondingly dimensioned cell culture spaces ("wells") having other dimensions, for example, larger electrode arrangements of "12-well" size and smaller electrode arrangements of "48-well" size. Thus, with a device according to the invention for contacting at least two electrode arrangements at least two, preferably four, different plate sizes may be contacted electrically in an advantageous manner.

LIST OF REFERENCE NUMBERS

1 Electrode arrangement
2 Electrode
3 Electrode
4 Electrode
5 Isolating material
6 Inner space
7 Container
8 Bottom area
9 Areas
10 Electrode arrangement
11 Electrode
12 Electrode
13 Electrode
14 Electrode
15 Isolating material
16 Inner space
17 Container
18 Bottom area
20 Electrode arrangement
21 Electrodes
22 Carrier
23 Base body
24 Border area
25 Underside
26 Isolating material
27 Spacer
28 Contact elements
29 Region
30 Upper side
31 End
32 Area
33 Face surface
40 Electrode arrangement
41 Electrode
42 Electrode
43 Electrode
44 Electrode
45 Space
46 Bottom area
47 Electrode arrangement
48 Active electrodes
49 Floating electrodes
50 Open switching devices
51 Closed switching devices
52 High voltage
53 Ground
54 Closed switching devices
55 Open switching devices
56 Active electrodes
57 Floating electrodes
58 Device
59 Switching device
60 Switching device
61 Switching device
62 Switching device
63 Active electrodes
64 Floating electrodes
65 Electrode arrangement
66 Electrode arrangement
67 Reception area
68 Electrodes
69 Electrodes
70 Contact points
71 Contact points
72 Contact points
73 Contact points
74 Electrode arrangement
75 Electrode arrangement
76 Reception area
77 Electrode arrangement
78 Electrode arrangement
79 Section
80 Section
81 Contact points
82 Contact points

The invention claimed is:

1. Method for applying at least three electric fields to adherent cells, comprising:
providing at least three electrodes,
providing a container having a bottom area,
providing said adherent cells which adhere to said bottom area,
applying a first electrical field to said adherent cells by applying voltage to at least two of said at least three electrodes, wherein said at least two electrodes are thus active electrodes,
subsequently applying at least a second electric field to said adherent cells,
wherein at least one of the two active electrodes of said first electrical field is, in said second electrical field, a floating electrode when the voltage is applied to generate said second electrical field, and applying further electric fields in said adherent cells until all electrodes that have been active when the first electric field was applied to said adherent cells have at least once been floating electrodes.

2. The method according to claim 1, wherein the at least three electrical fields are respectively generated by at least one voltage pulse wherein a time gap between the voltage pulses is at least 500 ms.

3. The method according to claim 2, wherein each electrical field is respectively generated by at least two voltage pulses, and wherein the time gap between the voltage pulses is at least 1 s.

4. The method according to claim 3, wherein the time gap between the voltage pulses is 1 to 10 s.

5. The method according to claim 1, wherein several reaction spaces are provided within said container within which the electric fields are respectively applied to adherent cells, and wherein a time gap between two voltage pulses for generating two electric fields within a first reaction space is utilized to generate at least one electric field within at least a second reaction space.

6. The method according to claim 1, wherein the electrodes and the adherent cells are separated from each other by a distance and the distance between the cells and the electrodes is adjusted to an empirically determined value.

* * * * *